(12) United States Patent
Walker

(10) Patent No.: US 12,290,432 B2
(45) Date of Patent: May 6, 2025

(54) SURGICAL FILAMENT SECUREMENT ASSEMBLIES AND PROCEDURES

(71) Applicant: PMSW RESEARCH PTY LTD, Bellevue Hill (AU)

(72) Inventor: Peter Walker, Bellevue Hill (AU)

(73) Assignee: PMSW RESEARCH PTY LTD, Bellevue Hill (AU)

( * ) Notice: Subject to any disclaimer, the term of this patent is extended or adjusted under 35 U.S.C. 154(b) by 747 days.

(21) Appl. No.: 17/633,125

(22) PCT Filed: Aug. 21, 2020

(86) PCT No.: PCT/AU2020/050870
§ 371 (c)(1),
(2) Date: Feb. 4, 2022

(87) PCT Pub. No.: WO2021/035288
PCT Pub. Date: Mar. 4, 2021

(65) Prior Publication Data
US 2022/0273420 A1 Sep. 1, 2022

(30) Foreign Application Priority Data
Aug. 23, 2019 (AU) ................. 2019903082

(51) Int. Cl.
*A61F 2/08* (2006.01)
*A61B 17/04* (2006.01)
(52) U.S. Cl.
CPC ..... *A61F 2/0811* (2013.01); *A61B 2017/0409* (2013.01); *A61B 2017/0414* (2013.01);
(Continued)

(58) Field of Classification Search
CPC ........ A61B 17/0401; A61B 2017/0409; A61B 2017/0412; A61B 2017/0414;
(Continued)

(56) References Cited

U.S. PATENT DOCUMENTS

2007/0142835 A1 6/2007 Green et al.
2008/0147063 A1 6/2008 Cauldwell et al.
(Continued)

FOREIGN PATENT DOCUMENTS

EP 3228256 A2 10/2017

OTHER PUBLICATIONS

International Search Report & Written Opinion dated Oct. 26, 2020 from corresponding PCT Application No. PCT/AU2020/050870.

*Primary Examiner* — Samuel S Hanna
(74) *Attorney, Agent, or Firm* — INNOVATION CAPITAL LAW GROUP, LLP; Vic Lin

(57) ABSTRACT

A surgical filament securement assembly has an anchor having a channel therethrough through which a surgical filament is passed. The surgical filament is tied to form a dilated knot having at least one throw around a dilater member at an entrance of the channel such that the surgical filament is able to run around the dilater member when a limb thereof is pulled in a first direction through the channel whilst the dilated knot remains in place. When the dilater member is pulled out from within the dilated knot, the dilated knot itself strangulates to form a tightened stopper knot. The channel has a diameter less than that of the tightened stopper knot such that the tightened stopper knot cannot pass through the entrance in the first direction.

21 Claims, 19 Drawing Sheets

(52) U.S. Cl.
CPC ............... *A61B 2017/0445* (2013.01); *A61B 2017/0458* (2013.01); *A61B 2017/0464* (2013.01); *A61F 2002/0817* (2013.01); *A61F 2002/0852* (2013.01)

(58) Field of Classification Search
CPC .... A61B 2017/0464; A61B 2017/0417; A61B 2017/0445; A61B 2017/0458; A61F 2/0811; A61F 2002/0817; A61F 2002/0852
See application file for complete search history.

(56) References Cited

U.S. PATENT DOCUMENTS

| | | |
|---|---|---|
| 2013/0261664 A1 | 10/2013 | Spenciner et al. |
| 2017/0000478 A1* | 1/2017 | Caborn .............. A61B 17/0483 |

* cited by examiner

SURGICAL FILAMENT SECUREMENT ASSEMBLIES AND PROCEDURES

FIELD OF THE INVENTION

This invention relates generally to a surgical filament securement assembly for tightening sutures.

BACKGROUND OF THE INVENTION

A common injury, especially among athletes, is partial or complete detachment or tearing of a tendon, ligament, meniscus or other soft tissue.

Remedial surgical intervention therefor includes use of suture anchors secured with arthroscopic knots.

Arthroscopic knot tying commonly involves slidably affixing a suture to an anchor wherein one limb thereof is passed through or over soft tissue to be repaired whereafter the two ends of the suture are tied together, thereby capturing the soft tissue in a loop and fastening the soft tissue to the bone via the anchor.

Surgeons typically tie the free ends using surgical sliding knots, such as the Tennessee Slider or Duncan Knot. However, to protect against loosening or slippage (referred to as "loop security") additional half hitches are thrown behind the tightened sliding knot.

However, sliding knots may be difficult to tie and secure and even fully tied knots may slip. Furthermore, the overall size of conventional sliding knots may be obstructive or intrusive especially in tight joints which may damage cartilage or tissue by abrasion.

US 20170000478 A1 (LINVATEC CORPORATION) 5 Jan. 2017 [hereinafter referred to as D1] discloses meniscal repair involving an anchor having a distal end having a distal slot extending proximally into the elongated body and a proximal end having a proximal slot extending distally into the body. The distal slot comprising a wide section and a narrow section, wherein the wide section has a width such that the suture is slidably accommodated therein and the narrow section has a width such that the suture is bound therein, and further wherein the wide section is disposed distally of the narrow section EP 3228256 A2 (DEPUY MITEK, LLC) 11 Oct. 2017 [hereinafter referred to as D2] discloses a surgical filament snare assembly including an anchor capable of being fixated in bone and having a filament engagement feature. A first filament has a noose on a first portion of at least a first limb and has a second portion connected to the filament engagement feature of the anchor. At least one free filament limb is capable of being passed through tissue to be repaired and has at least one end passable through the noose to enable incremental tensioning of the tissue after the anchor is fixated in bone. As such, the noose strangulates the free filament limb when tension is applied to at least one of the free filament limb and the noose.

US 20130261664 A1 (SPENCINER et al.) 3 Oct. 2013 [hereinafter referred to as D3] discloses a suture anchor having an anchor body with a passage extending from a proximal end toward a distal end. A knot patency element disposed within the passage holds a removable sliding knot formed, using the surgical filament. A tightening limb of the sliding knot enables the user to tighten the sliding knot against an object extending through a capture loop to secure the object to the anchor.

US 20070142835 A1 (GREEN MICHAEL L et al.) 21 Jun. 2007 [hereinafter referred to as D4] discloses a bone anchor having pre-attached suture material. After insertion, lateral wings can be deployed on the bone anchor to prevent anchor pull-out. The suture may be attached at the tip of the anchor by tying it to a wire hook secured in a cavity in the anchor tip. The anchor may be inserted and deployed using an anchor inserter that is configured to apply an axial force to the anchor, thereby deforming the anchor to form the lateral wings

SUMMARY OF THE DISCLOSURE

There is provided herein a surgical filament securement assembly comprising an anchor capable of being fixated in bone. The anchor has a channel therethrough (such as a passage, slot or the like) through which a surgical filament is passed.

The surgical filament is tied to form a dilated knot having at least one throw around a dilater member at an entrance of the channel such that the surgical filament is able to run around the dilater member when a limb thereof is pulled in a first direction into the channel such that the dilated knot remains in place at the entrance.

However, when the dilater of member is removed from the dilated knot, the dilated knot strangulates to form a tightened stopper knot. The tightened stopper knot has a diameter greater than that of the entrance of the channel such that the stopper knot cannot pass therethrough in the first direction to thereby prevent the limb from continuing running in the first direction.

The dilater member can be a further suture passing through the dilated knot or alternatively a rigid member including one formed by an insertion tool and either orientated longitudinally or orthogonally so as to allow for the pull-off or twist off engagement.

The dilated knot remains at the same position whilst running around the dilater member, unlike the conventional slider knots alluded which require manual sliding or use or slider knot pushing devices.

The anchor may comprise a bore non-coaxially adjacent the channel at the entrance. As such, the anchor can be inserted using an inserter without predrilling and tied off in the aforedescribed manner. The bore may allow the insertion of the anchor with an insertion tool without predrilling and the channel adjacent the bore may allow the running of the suture through the channel around the dilated knot at the entrance thereof (such as around a dilater member integrally formed at a tip of the insertion tool) whilst the insertion tool is engaged within the bore.

In contradistinction to the prior art, with reference to D1, D1 uses a cleat-type anchor 10 which uses a narrow section 50 of a slot 40 to entrap the suture. D1 further teachers twisting of the suture to increase holding strength. D1 however does not teach a knot having at least one throw. The suture of D1 is rather twisted around the shaft 85. D1 furthermore does not show the dilated knot having at least one throw running around a dilater member at an entrance to the channel and the pulling of the suture in the first direction into the channel such that the dilated knot remains in place at the entrance. D1 furthermore does not show the pulling of the dilator member from the knot (having at least one throw) so that the dilated knot strangulates to form a stopper knot having a diameter greater than the channel such that the stopper knot cannot pass through the entrance in the first direction to thereby prevent the limb from continuing running in the first direction.

With reference to FIG. 1 of D2, D2 shows an anchor 12 having a filament 14 having a distal permanent knot 32 and a proximal noose 30. A threader filament 46 is passed through the noose 30, the threader filament 46 having a distal noose 52. A second filament 60 engaging tissue is passed through the distal noose 52 of the threader filament 46. The threader filament 46 is then pulled to pull the second filament 60 through the proximal noose 30 of the anchor 12. The threader filament 46 is then removed and a stopper knot 70 tied in the second filament 60 which then slides down towards the anchor numeral 12 for securement (see FIGS. 8-10).

However, D2 similarly does not disclose an anchor having a channel having a dilated knot having at least one throw running round a dilator member at an entrance thereof which remains statically in place as the suture is pulled into the channel let alone a dilator member which is pulled from the dilated knot at the entrance such that the knot strangulates to a tightened stopper knot which cannot pass through the entrance in the first direction to thereby prevent the limb from continuing running in the first direction. Rather, D2 uses a conventional slider knot which is specifically unlike the dilated knot which remains in place at the entrance of the present arrangements.

With reference to D3, D3 discloses an anchor having a slipknot 80 around a cylinder therein. A suture 92 securing tissue can be passed through a capture loop 84 of the slipknot. A tightening limb 88 can be pulled which pulls the slipknot from the cylinder, thereby allowing for the tightening the slipknot 80 around the captured suture 92. The captured suture 92 can then be pulled into or from a distal end of the anchor using the shortening limb 54. However, D3 similarly does not disclose an anchor having a channel having a dilated knot having at least one throw running around a dilator member at an entrance thereof which remains statically in place as the suture is pulled into the channel let alone a dilator member which is pulled from the dilated knot at the entrance such that the knot strangulates to a tightened stopper knot which cannot pass through the entrance in the first direction. Rather, D3 uses a slipknot which does move which is unlike the dilated knot which remains in place of the present arrangements. Furthermore, the slipknot of D3 does not have a diameter greater than the channel, rather the slipknot of D3, when tightened, can pass through the channel of the anchor.

With reference to D4, D4 describes an insertion tip having a cavity 108 therein within which a suture knot is formed to prevent being pulled through the shaft 110 thereof. FIGS. 4B and 4C show the use of a wire hook to hold the knot within the cavity 108.

However, D4 similarly does not disclose an anchor having a channel having a dilated knot having at least one throw running around a dilator member at an entrance thereof which remains statically in place as the suture is pulled into the channel let alone a dilator member which is pulled from the dilated knot at the entrance such that the knot strangulates to a tightened stopper knot which cannot pass through the entrance in the first direction.

According to D4, the wire hook 122 remains in place and is not pulled from the knot. Furthermore, according to D4, the wire hook 122 does not function as a dilator member because the suture does not to run around the wire hook 122.

According to one aspect, there is provided a surgical filament securement assembly comprising an anchor, the anchor having a channel therethrough through which a surgical filament is passed, the surgical filament tied to form a dilated knot having at least one throw around a dilater member at an entrance of the channel such that the surgical filament is able to run around the dilater member when a limb thereof is pulled in a first direction through the channel whilst the dilated knot remains in place at the entrance and wherein, when the dilater member is pulled out from within the dilated knot, the dilated knot itself strangulates to form a tightened stopper knot and wherein the channel has a diameter less than that of the tightened stopper knot such that the tightened stopper knot cannot pass through the entrance in the first direction.

The channel may run between a proximal face and a side of the anchor.

The entrance may be at the proximal face.

The anchor may comprise a further channel for a further surgical filament through the proximal face.

The dilater member may pass through both dilated knots of the surgical filament and the further surgical filament.

The dilater member may comprise a dilater filament.

The dilater member may comprise a rigid member.

The dilater member may be orientated longitudinally with respect to the elongate axis of the anchor and wherein pulling the dilater member from the dilated knot may comprise pulling the dilater member away from the anchor.

The dilater member may be orientated orthogonally with respect to the elongate axis of the anchor and wherein pulling the dilater member from the dilated knot may comprise twisting the dilater member with respect to the anchor.

The dilated knot may be a single throw knot.

The dilated knot may be a overhand knot.

The dilated knot may be a multiple throw knot.

The assembly may further comprise an insertion instrument and wherein the insertion instrument may comprise the dilater member.

The dilater member may be integrally formed in a distal edge of the insertion instrument.

The dilater member may be orientated longitudinally with respect to an elongate axis of the insertion instrument and may be formed by parallel longitudinal cuts either side thereof.

The dilater member may be orientated substantially orthogonally with respect to an elongate axis of the insertion instrument and may be formed by a longitudinal cut through the distal edge which transitions at a right angle to an orthogonal cut adjacent the dilater member.

The anchor may comprise bore non-coaxially adjacent the channel at the entrance.

The assembly may further comprise an insertion instrument comprising an insertion rod which engages a bore of the anchor.

The bore may comprise an interior dogleg around the channel and wherein the insertion rod transitions diagonally through the interior dogleg to engage the anchor.

The anchor may comprise a side opening and wherein the insertion rod transitions diagonally from the side opening.

The rod may comprise a head which may be able to fit diagonally through the interior dogleg as the rod passes from the proximal side opening.

The head may bear against opposite inner surfaces of the bore once past the dogleg.

The insertion instrument may comprise an orthogonal bearing face which bears against a proximal face of the anchor.

The assembly may further comprise a distal anchor affixed to another limb of the surgical filament.

The surgical filament may be a fixed through a side entrance of the distal anchor.

The anchor and the distal anchor may comprise a bore therethrough for the slidable receipt of a tip of an insertion instrument therethrough.

The tip may be slidably retained within a coaxial rod and may comprise a longitudinal member slidably retained within a side channel thereof, the longitudinal member comprising a bearing face which bears against the anchor.

According to a further aspect, there is provided a method of securing an anchored surgical filament, the method comprising passing the surgical filament through a filament channel of an anchor, tying a dilated knot having at least one throw around a dilater member at an entrance of the filament channel, pulling a limb of the surgical filament in a first direction through the channel such that filament runs around the dilater member whilst the dilated knot remains in place at the entrance and pulling the dilater member out from within from the dilated knot such that the dilated knot itself strangulates to form a tightened stopper knot at the entrance having a diameter greater than that of the entrance such that the tightened stopper knot cannot pass through the entrance in the first direction.

Other aspects of the invention are also disclosed.

BRIEF DESCRIPTION OF THE DRAWINGS

Notwithstanding any other forms which may fall within the scope of the present invention, preferred embodiments of the disclosure will now be described, by way of example only, with reference to the accompanying drawings in which:

FIGS. 6-9C illustrate a surgical filament securement assembly comprising a pusher tool in accordance with an embodiment;

DESCRIPTION OF EMBODIMENTS

Figure 1:
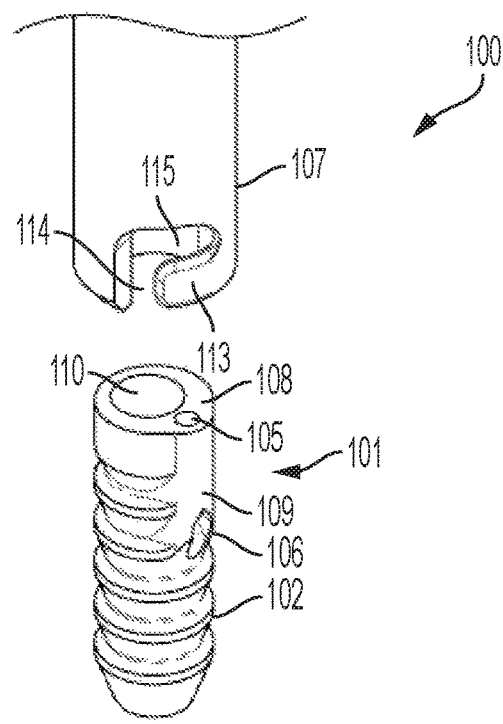
FIGS. 1-5 show a surgical filament securement assembly in accordance with an embodiment.
Figure 2:
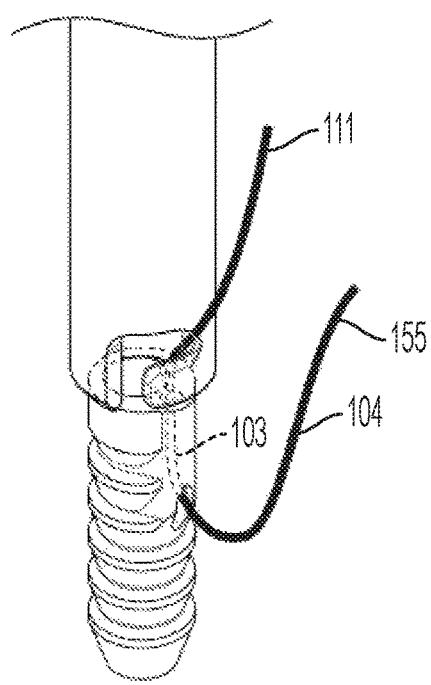

In accordance with a first embodiment of FIGS. 1-5, a surgical filament securement assembly 100 comprises an anchor 101 capable of being fixated in bone. The anchor 101 may be generally elongate, cylindrical and comprise exterior interference members 102 for affixation within bone.

The anchor 101 comprises a filament channel 103 between a first entrance 105 and a second entrance 106 therethrough through which a surgical filament 104 is passed. In alternative embodiments, the channel 103 may take the form of a slot.

The first entrance 105 may be orientated longitudinally through a proximal face 108 of the anchor 101. The second entrance 106 may be orientated at an angle through a lateral side 109 of the anchor 101.

The anchor 101 may comprise a bore 110. In embodiments, a rod of an inserter or pusher tool may be inserted into the bore 110 for insertion.

The bore 110 and the filament channel 103 may be non-coaxially (i.e. eccentrically) aligned adjacent each other at the proximal face 109 as shown in FIG. 1.

The surgical filament 104 passes through the channel 103, thereby defining a first limb 111 and a second limb 155. Generally, the second limb 155 passes through or over the tissue to be repaired.

Figure 3:
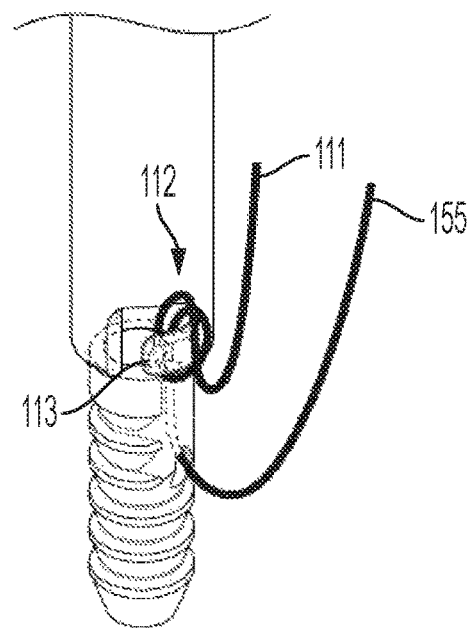

With reference to FIG. 3, the first limb 111 is tied to form a dilated knot 112 around a dilater member 113.

In the embodiment shown in FIGS. 1-5, the dilater member 113 is rigid and integrally formed within a distal end of an insertion tool 107. Furthermore, the dilater member 113 may be orientated orthogonally with respect to an elongate axis of the anchor 101 or tool 107 by a vertical cut 114 which transitions to a lateral cut 115 at a right angle.

Prior insertion, the insertion instrument 107 may be preloaded with the anchor 101 and the dilated knot 112.

The dilated knot 112 shown has one throw and may be a simple overhand knot. In other embodiments, the dilated knot 112 may comprise multiple throws and multiple loops.

The dilated knot 112 is able to run around the dilater member 113 when either limb 111, 155 of the surgical filament 104 is pulled.

In one application, the second limb 155 passing from the second entrance 106 loops around or through the tissue to be repaired and the first limb 111 is pulled to tighten the second limb 155.

The first limb 111 may be pulled in general alignment with the longitudinal axis of the anchor 101 and/or insertion tool 107 by hand, or mechanical cleat or ratchet mechanism in embodiments.

As the limb 111 is pulled, the surgical filament 104 runs around the dilater member 113 with the dilated knot 112 remaining in position at the dilater member 113.

Figure 4:
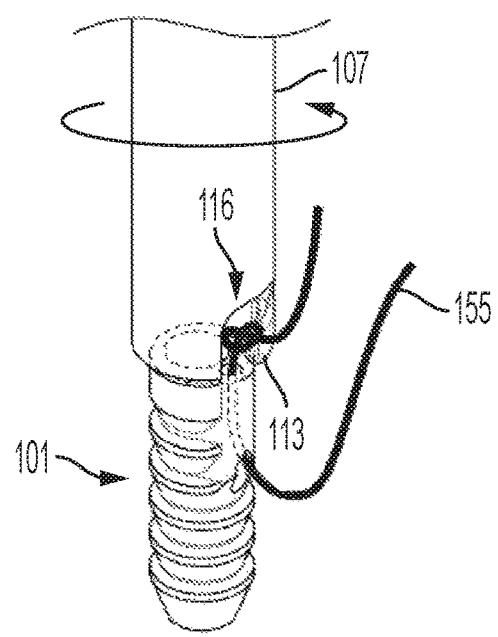
Figure 5:
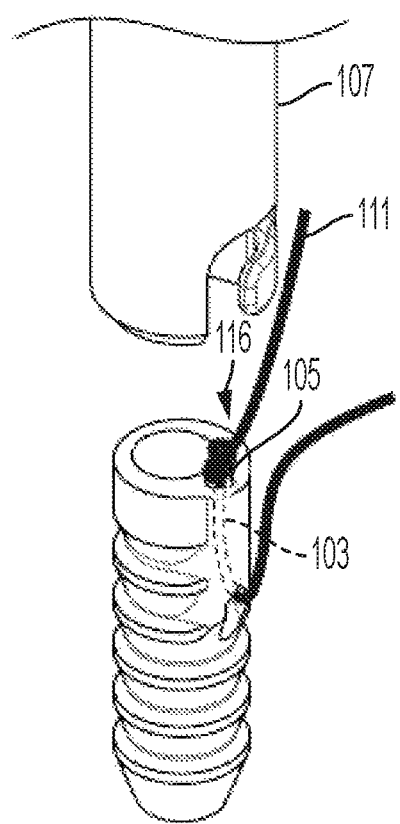
Figure 6:
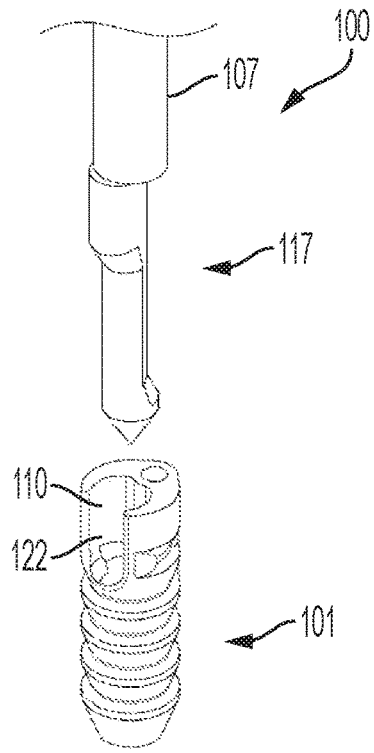
Figures 7, 8:
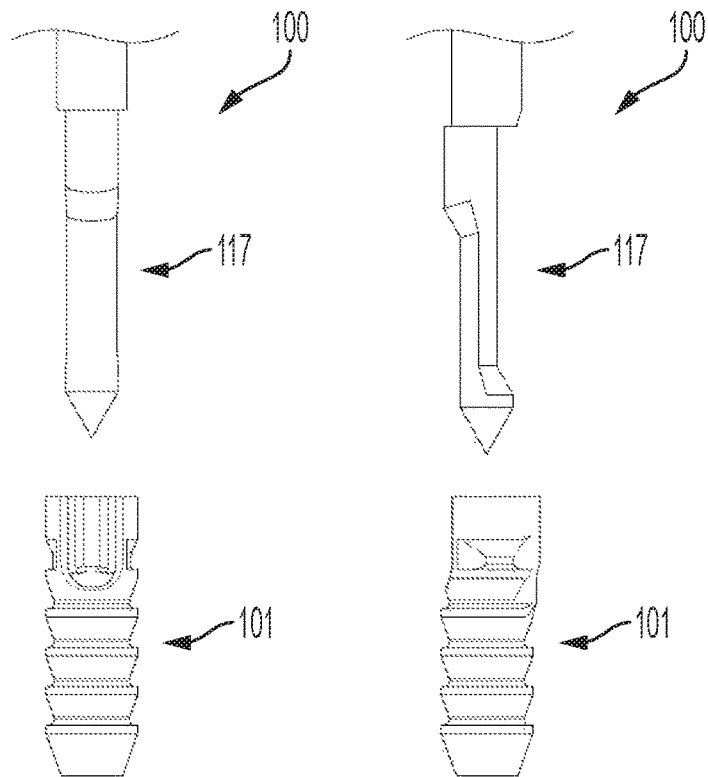

When the second limb 155 is sufficiently tightened, the insertion tool 107 may be rotated with respect to the anchor 101 in the manner illustrated in FIG. 4 such that the orthogonally orientated dilater member 113 is pulled from the dilated knot 112.

The removal of the dilater member 113 allows the dilated knot 112 to strangulate, thereby forming a tightened stopper knot 116 in the first limb 111 at the first entrance 105.

The filament channel 103 has a diameter less than that of the tightened stopper knot 116 such that the stopper knot 116 cannot pass into the channel 103 at the first entrance 105.

The insertion instrument 107 can then be removed after the formation of the stopper knot 116 and the first limb 111 trimmed.

In embodiments, the orthogonally orientated dilater member 113 may be angled downwardly to terminate at the bottom edge of the insertion tool 107 so as to form the tightened stopper knot 116 closer to the entrance 105.

In embodiments the insertion tool 107 comprises a cutting mechanism (not shown) which cuts the limb 111 above the stopper knot 116.

In embodiments, a cutting mechanism is formed by the longitudinal channel 115 transitioning also in an opposite direction with respect to the longitudinal channel 114 and having a sharpened cutting edge at a terminus thereof. As such, as the insertion tool 107 is rotated in the manner shown in FIG. 4, the sharpened cutting edge moves across to cut the first limb 111.

Figure 28:
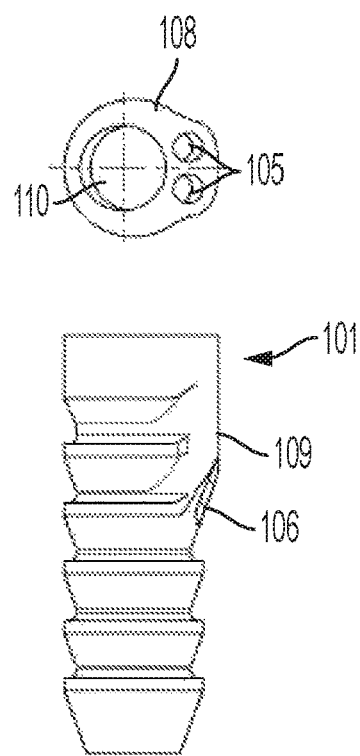
FIGS. 28-29 illustrate an anchor in accordance with an embodiment.
Figure 29:
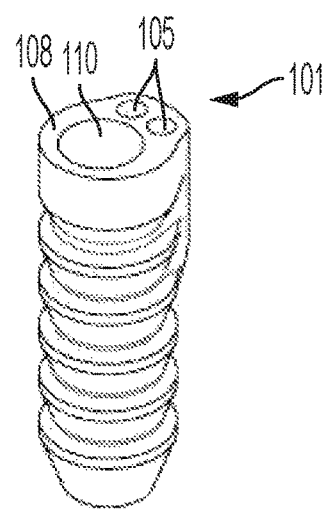

FIGS. 28 and 29 illustrate an embodiment of the anchor 101 wherein the anchor 101 comprises a pair of channels 103 for a pair of respective surgical filaments 104. Each first entrance 105 may lead to the same or separate second entrances 106 through the lateral side 109 of the anchor 101. The pair of first entrances 105 may similarly be arranged adjacent the insertion tool engagement aperture 110.

In accordance with the embodiment of FIGS. 28, 29, the dilater member 113 may pass through both dilated knots 112 of the pair of surgical filaments 104, which, when pulled therefrom, allows both dilated knots 112 to strangulate. In alternative embodiments, separate dilater members 130 may be provided for each dilated knot 112.

FIGS. 6-9 illustrate an embodiment wherein the insertion tool 107 comprises a dogleg shaped engagement rod 117 which engages within the bore 110 of the anchor 101.

With reference to FIG. 9, the bore 110 forms a corresponding internal dogleg 118 so as to transition around the filament channel 103 in the manner shown and may have a side opening 122. The side opening 122 allows the insertion tool 107 to be of sufficient diameter for insertion resilience yet allowing adjacent space for the channel 103.

Figures 9A, 9B, 9C:
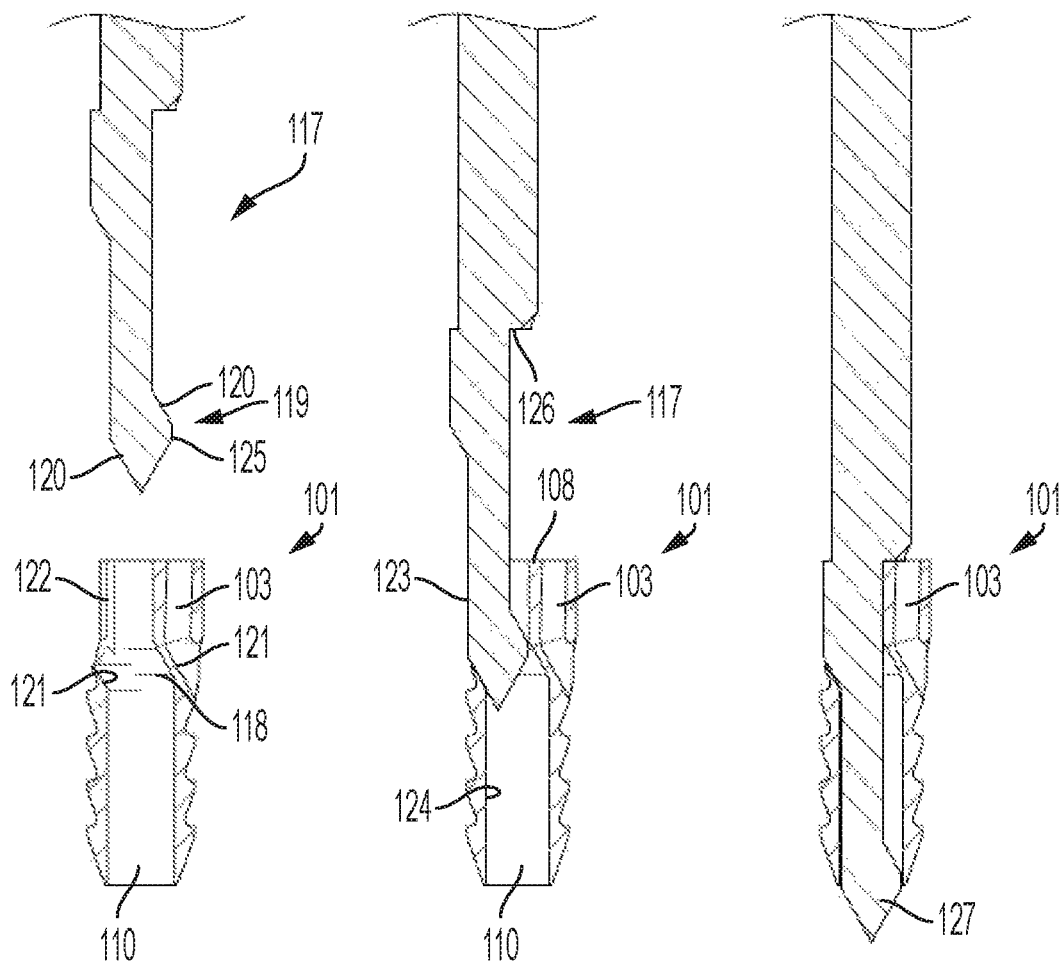

The engagement rod 117 may comprises a distal head 119 comprising angled faces 120 which are able to fit diagonally between interior faces 121 of the dogleg 118 of the bore 110 as is illustrated in FIG. 9B as the rod 117 passes from the side opening 122.

The shaped engagement rod 117 moves diagonally into substantial coaxial alignment with the anchor 101 and a rear face 123 thereof may bear against an inner surface 124 of the bore 110 and a lateral apex 125 of the head 119 may bear against an opposite inner surface 124 to hold the rod 117 in alignment at two points within the bore 110.

The rod 117 may comprises an orthogonal bearing face 126 which presses against the proximal face 108 of the anchor 101 to drive the anchor 101 forwardly. A point 127 of the rod 117 may extend through the anchor 101 to assist the penetration thereof during insertion.

The rod 117 may comprise the dilater member 113 for the formation of the dilated knot 112 in the aforedescribed manner.

The present techniques will now be described with reference to an exemplary application of meniscal repair shown in FIGS. 10-27.

In accordance with this embodiment, meniscal repair apparatus 128 may comprise an insertion instrument 129 comprising a handle 130. The insertion instrument 129 may comprise an insertion rod 131 comprising a proximal and distal anchor toggles 132 retained at a distal end thereof.

Figure 10:
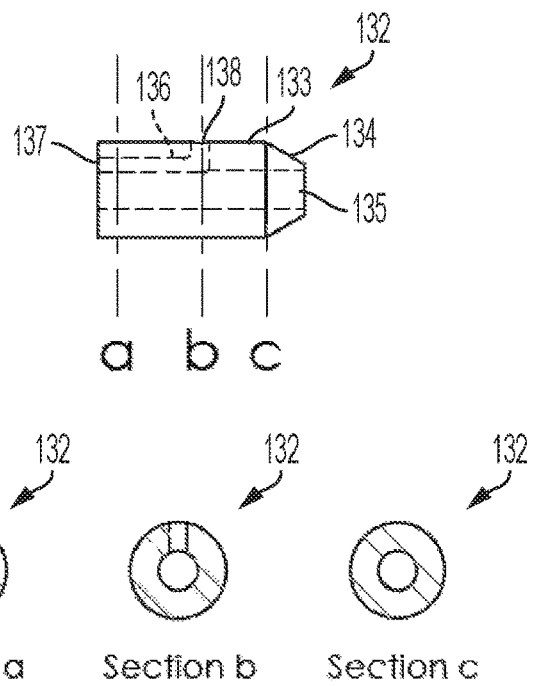
FIGS. 10-19 illustrate apparatus for meniscal repair in accordance with an embodiment.
Figure 11:
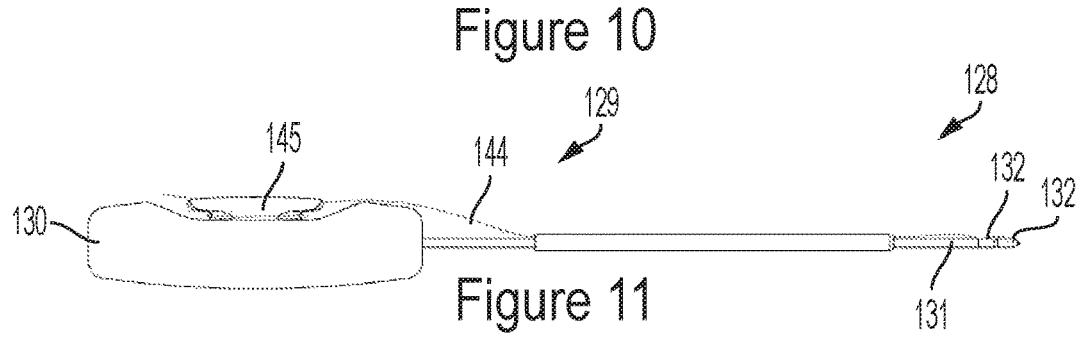

With reference to FIG. 10, an anchor toggle 132 may comprise a cylindrical body 133 which may comprise a distal taper 134. A bore 135 for retaining the insertion rod 131 may run through the body 133.

The anchor toggle 132 comprises a filament channel 136 which transitions through 90° from a rear entrance 137 to a side entrance 138. As is evident from section A, the rear entrance 107 may intersect the bore 135

Figures 12, 13:
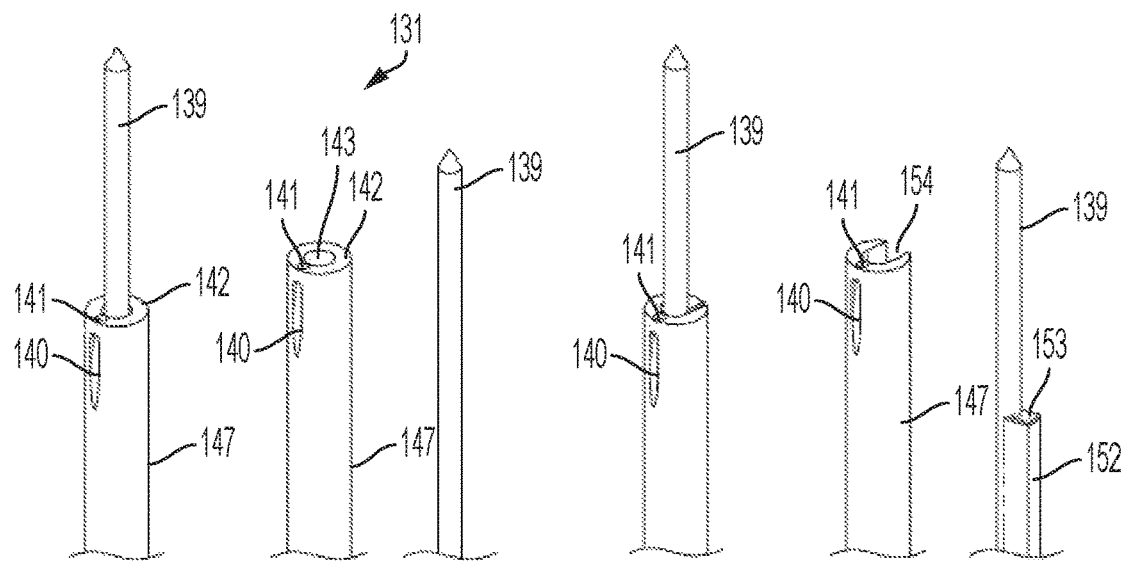
Figure 14:
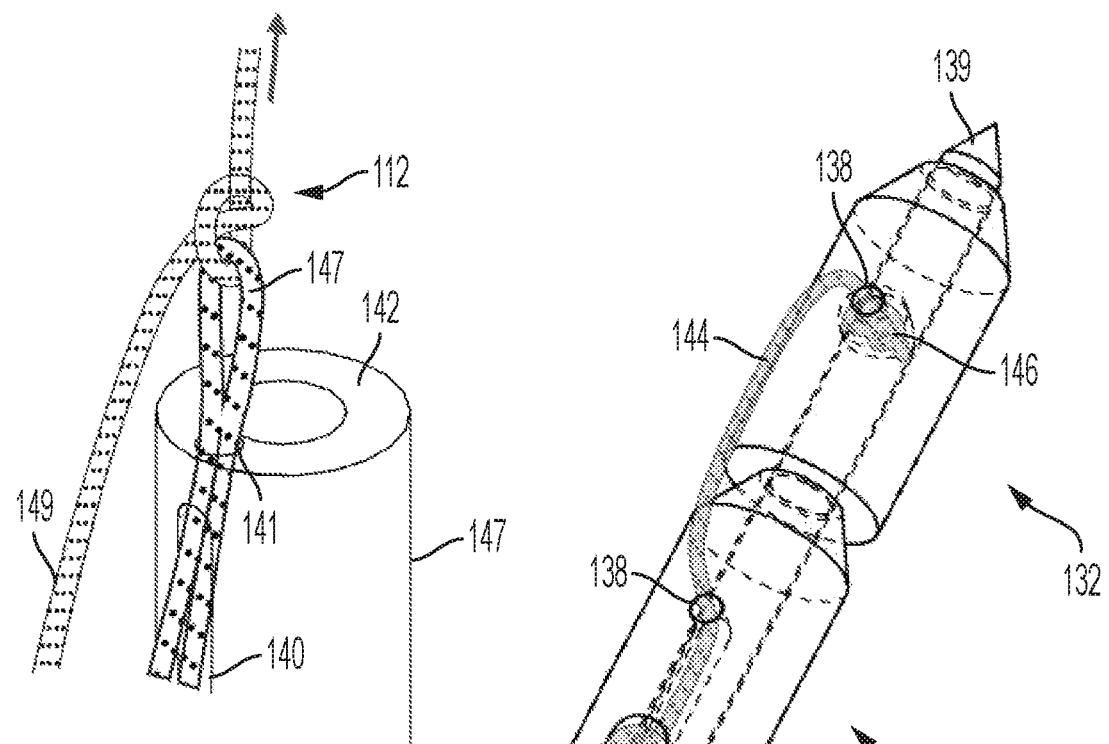

With reference to FIG. 12, the insertion rod 131 may comprise a cannulated rod 147 and a needle 139 slidably and coaxially retained within a bore 143 thereof. The cannulated rod 147 may comprise an angled lead-in entrance 140 and an exit 141 through a distal face 142 thereof. The exit 141 may be non-coaxially aligned adjacent the bore 143. A surgical filament 144 may run through the angled lead-in entrance 140 via the exit 141 to the anchor toggles 132. A proximal end of the surgical filament 144 may be retained around a handle cleat 145 or other similar mechanism.

FIG. 13 illustrates an embodiment wherein the 139 comprises an integral longitudinal member 152 defining a distally orientated bearing face 153 which slides within a corresponding side channel 154 of the cannulated rod 147. The distally orientated bearing face 153 may bear against the proximal face of the anchor toggle 132 when the cannulated rod 147 is being retracted.

Figure 15:
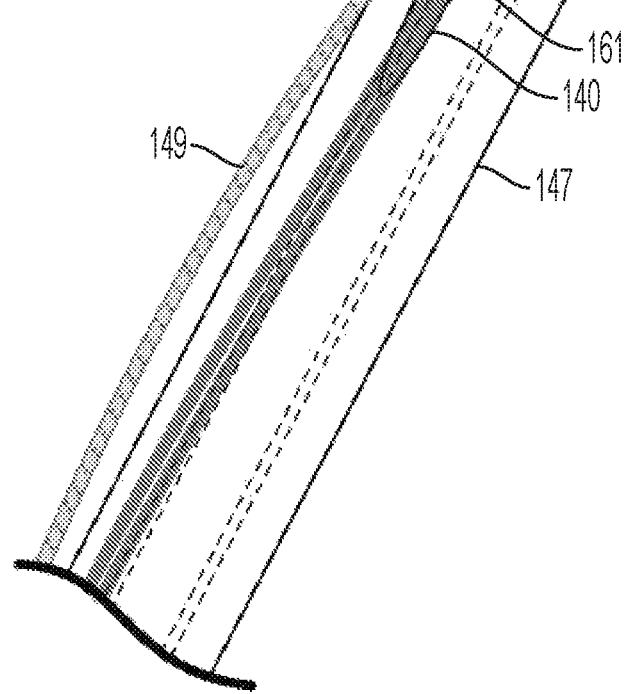

FIG. 15 illustrates an embodiment wherein the proximal and distal anchor toggles 132 are coaxially retained on the needle 139 and bear rearwardly on the cannulated rod 147.

A surgical filament 144 is retained to the distal anchor toggle 132 by way of a distal tightened knot 146 or other fixation method which leads from the side entrance 138 of the distal anchor toggle 132.

The surgical filament 144 passes through the side entrance 138 of the proximal anchor toggle 132. Whereas FIG. 15 shows the filament 144 exiting the side entrance 138 and travelling through a central bore of the proximal anchor toggle 132, in alternative embodiments, the filament 144 may enter the side entrance 138 and travel through a centre bore of the proximal anchor 132 thereinfront. A dilated knot 112 is then formed about a dilater suture 161 which is looped and passes between the lead-in side entrance 140 and from the exit 141.

As such, the suture 144 may be tightened by pulling the proximal limb 149 thereof. The dilated knot 112 runs around the dilater suture 161. Once the anchor toggles 132 are positioned and the surgical filament 144 is sufficiently tightened, the dilater suture 161 may be released by freeing one limb thereof while pulling on the other such that the dilater suture 161 is pulled from the dilated knot 112, thereby allowing the dilated knot 112 to strangulate, thereby forming the tightened stopper knot at the rear entrance 137 of the proximal toggle anchor 132.

Figures 16, 17:
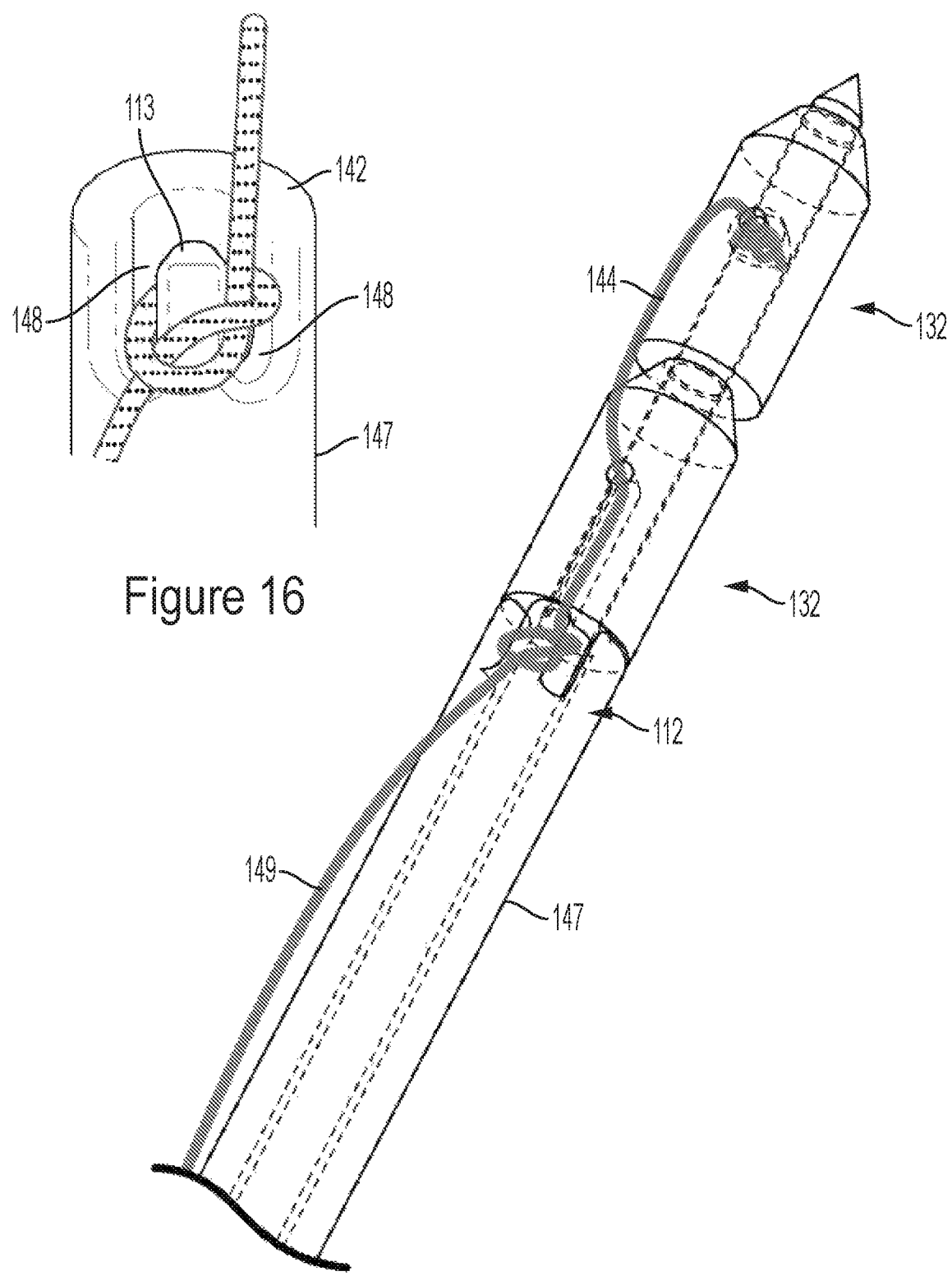
Figure 18:
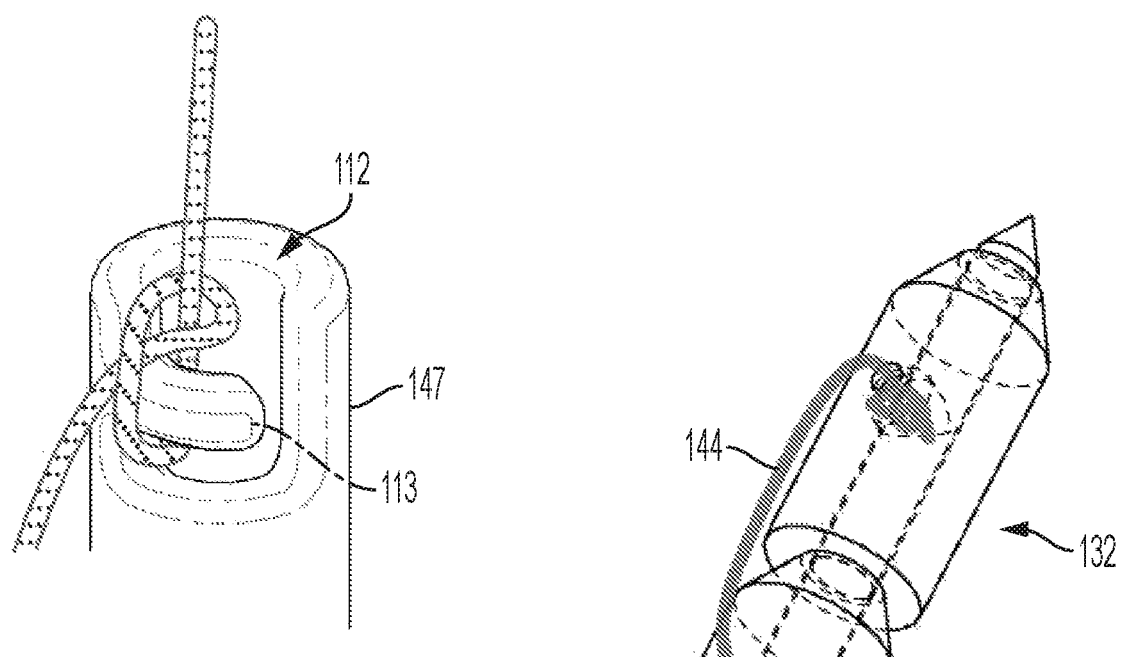

FIG. 17 shows an alternative embodiment of a similar configuration as that of FIG. 15 but wherein the cannulated rod 147 comprises a dilater member 113 which is orientated longitudinally. The dilater member 113 may be formed by longitudinal side cutouts 148 either side thereof through the distal face 142 of the cannulated rod 147.

The dilated knot 112 is formed around the longitudinally orientated dilater member 113 such that the proximal limb 149 thereof can be pulled to tighten the suture 144. The suture 144 runs around the longitudinal dilater member 113 with the dilated knot 112 remaining in position.

When the surgical filament 144 is sufficiently tightened, the cannulated rod 147 is pulled away from the proximal anchor toggle 132 such that the longitudinally orientated dilater member 113 is pulled from the dilated knot 112, thereby allowing the dilated knot 112 to strangulate, thereby forming the tightened stopper knot at the proximal entrance 137 of the proximal anchor toggle 132.

Figure 19:
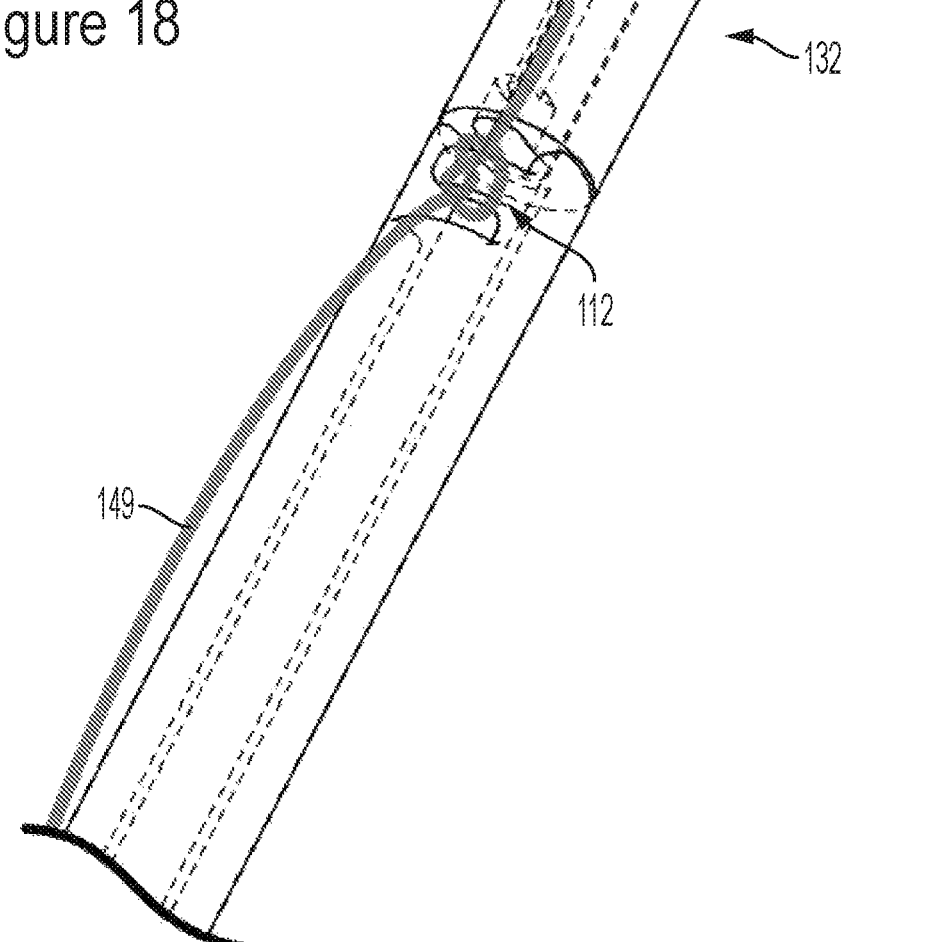

FIG. 19 illustrates a similar embodiment but wherein the cannulated rod 147 comprises an orthogonally orientated dilater member 113 having the dilated knot 112 formed therearound. In a similar manner, the suture 144 can be tightened by pulling the limb 149 thereof wherein the filament 144 runs freely over the orthogonally orientated dilater member 112 with the dilated knot 112 remaining in position. When the surgical filament 144 is sufficiently tightened, the cannulated rod 147 may be twisted to pull the orthogonally orientated dilater member 113 from the dilated knot 112, thereby allowing the dilated knot 112 to strangulate, thereby forming the tightened stopper knot at the proximal entrance 137 of the proximal anchor toggle.

Figure 20:
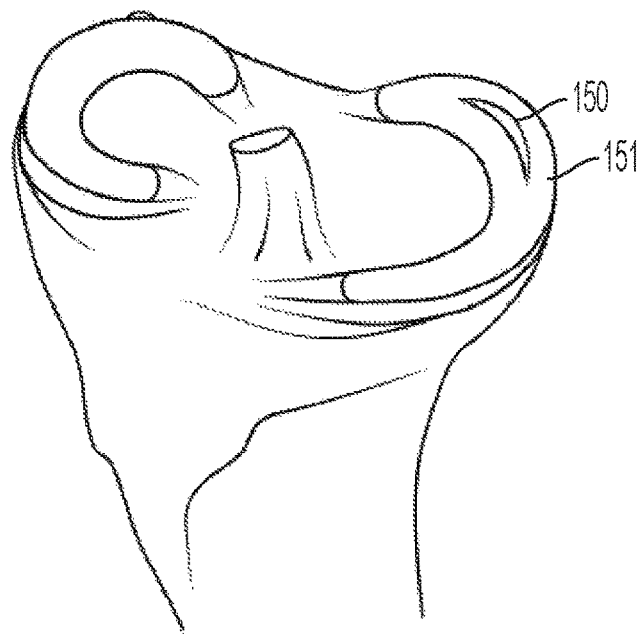
FIGS. 20-27 illustrate a meniscal repair procedure in accordance with an exemplary embodiment.
Figure 21:
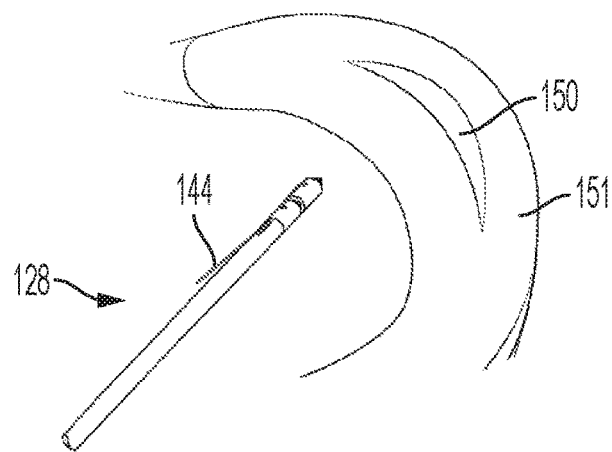

With reference to FIGS. 20 and 21, for the repair of a meniscal tear 150, the apparatus 128 may be preloaded with the proximal and distal anchor toggles 132 and the suture 144 in the aforedescribed manners of FIG. 15, 17 or 19.

Figure 22:
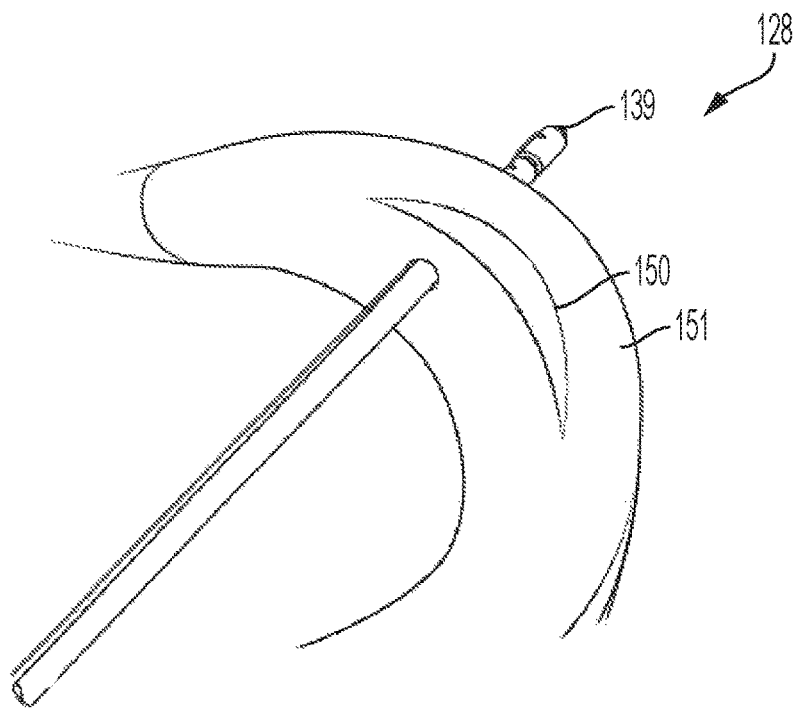

With reference to FIG. 22, the apparatus 128 may be pushed through the meniscus 151 from an inner side to an outer side at one end of the tear 150.

Figure 23:
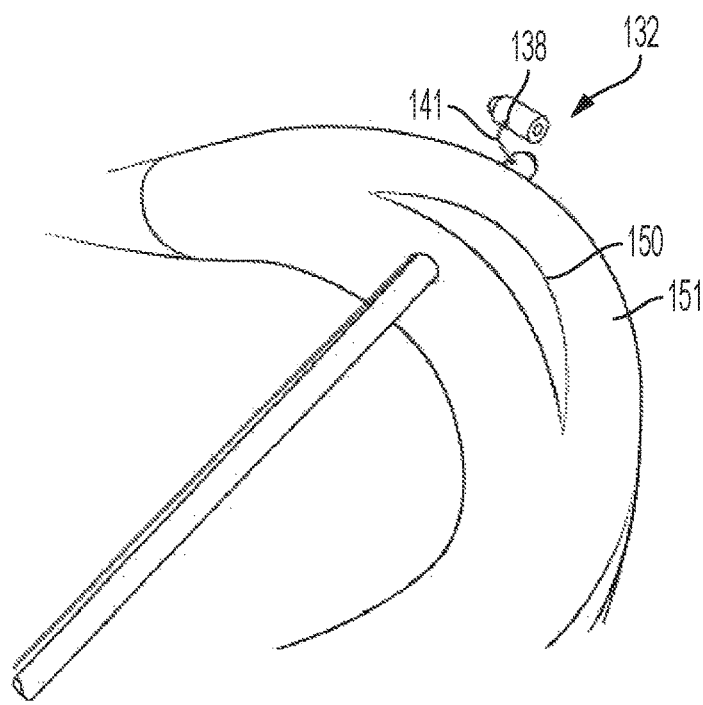

With reference to FIG. 23, the needle 139 is pulled rearwardly and the cannulated rod 147 is held in place such that the distal anchor toggle 132 is allowed to detach from the needle 139 to fix within the soft tissues. As alluded to above, the cannulated rod 149 may slide rearwardly with respect to the needle 139 such that the bearing face 153 thereof pushes the anchor toggles 132 away.

As the surgical filament 141 extends from the side entrance 138 of the distal anchor toggle 132, the distal anchor toggle 132 rotates through 90° when tension is applied to the surgical filament 141.

Figure 24:
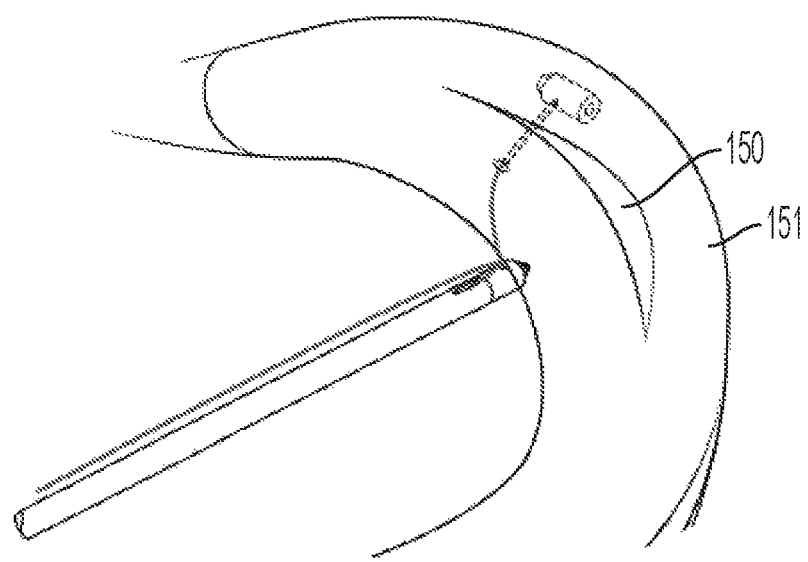
Figure 25:
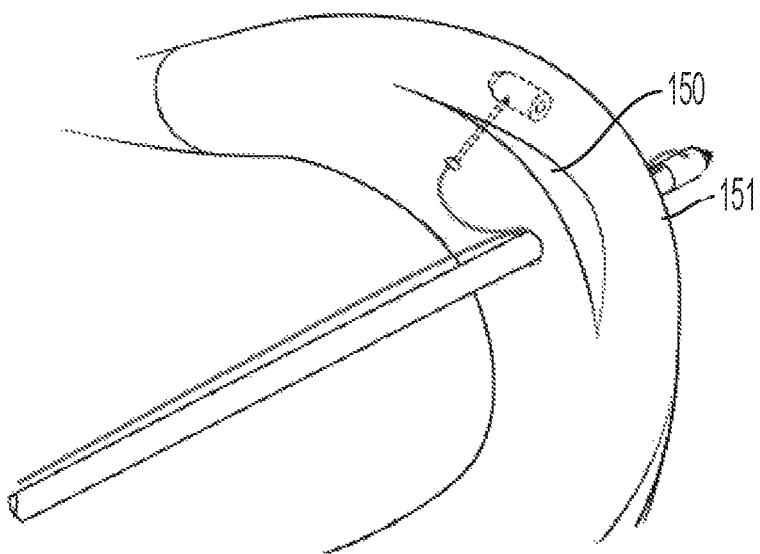

With reference to FIGS. 24 and 25, the apparatus 128 is pulled back into the joint and then reinserted through the meniscus 151 across the tear 150.

Figure 26:
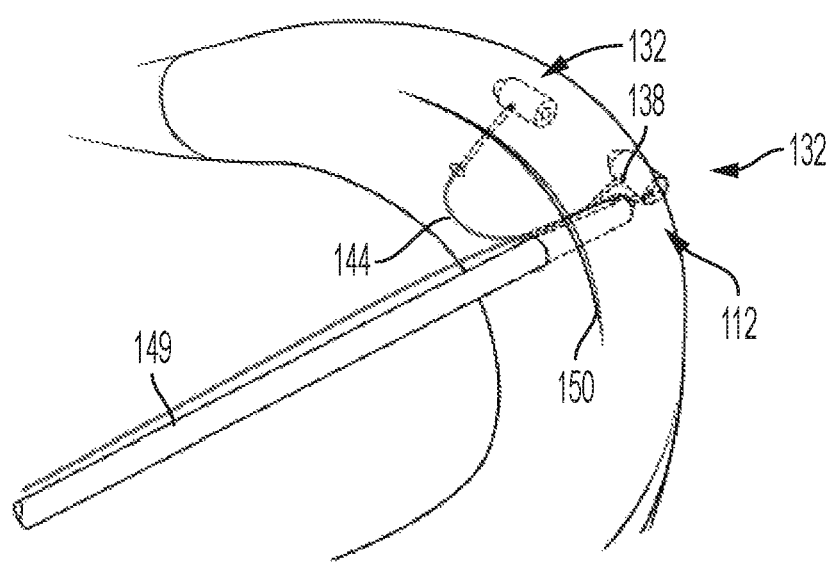
Figure 27:
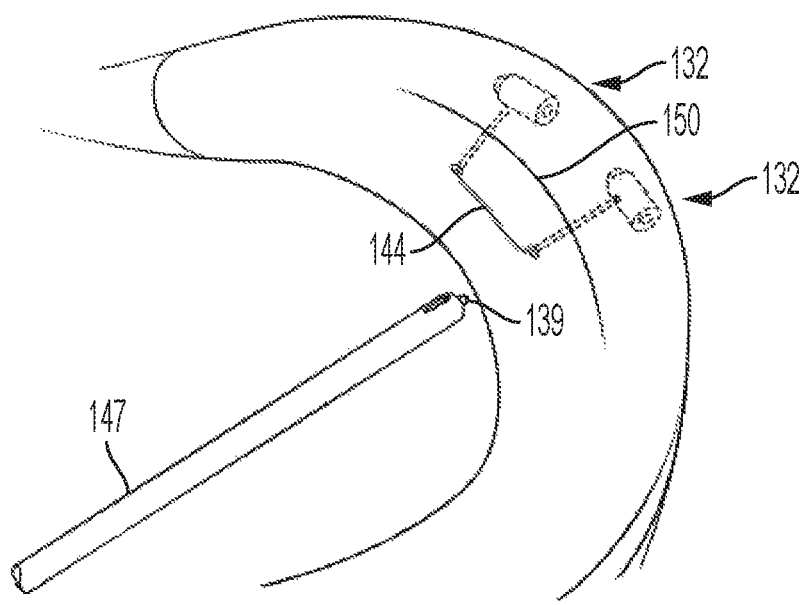

With reference to FIG. 26, the proximal toggle is allowed to disengage from the needle 139 in a similar manner.

The dilated knot 112 at the proximal entrance 137 of the proximal anchor toggle 132 is tightened by pulling the proximal limb 149 of the suture 144 such that the surgical filament 144 tightens between the anchor toggles 132. As the surgical filament 144 also passes through the side entrance 138 of the proximal anchor toggle 132, the proximal anchor toggle 132 also rotates through 90° such that each anchor toggle 132 bears sideways against the outer edge of the meniscus 151, thereby cooperating with the opposite suture loop to pull the tear 150 closed.

The cannulated rod 147 counteracts the pulling force on the proximal limb 149, thereby not pulling the anchor toggle 132 from the meniscus 151.

Once the dilated knot 112 is sufficiently tightened, the dilater member 113 is pulled from the dilated knot 112 such that the dilated knot 112 strangulates to form a tightened stopper knot at the proximal entrance 137 of the proximal anchor toggle 132.

The proximal limb 149 of the suture 144 is then cut and the cannulated rod 147 and needle 139 retrieved, thereby leaving the anchor toggles 132 and tightened suture loop in place holding the meniscal tear 150 closed.

Multiple anchor toggles 132 may be deployed in this manner if needs be, the last of which strangulates the dilated knot 112 in the aforedescribed manner.

Figure 30:
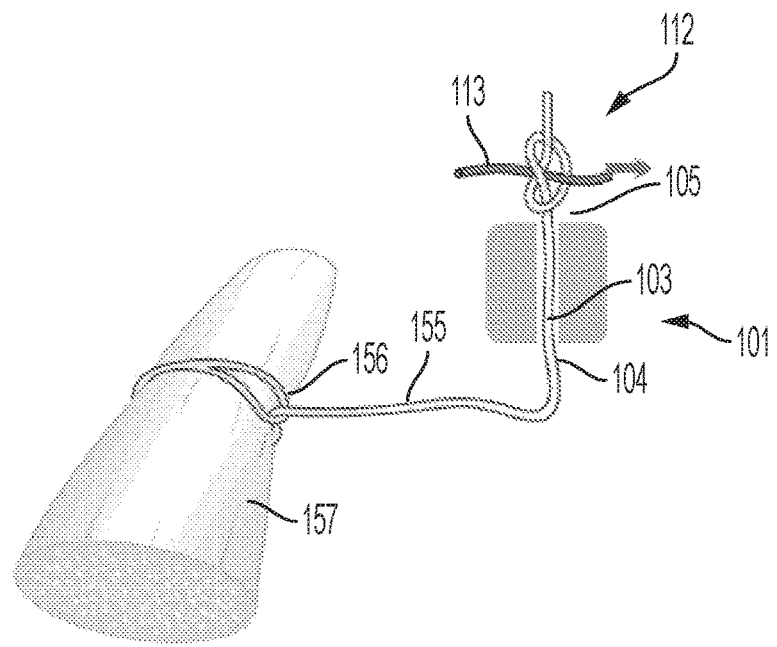
FIGS. 30-31 illustrate utilisation of the surgical filament securement assembly in accordance with an embodiment.
Figure 31:
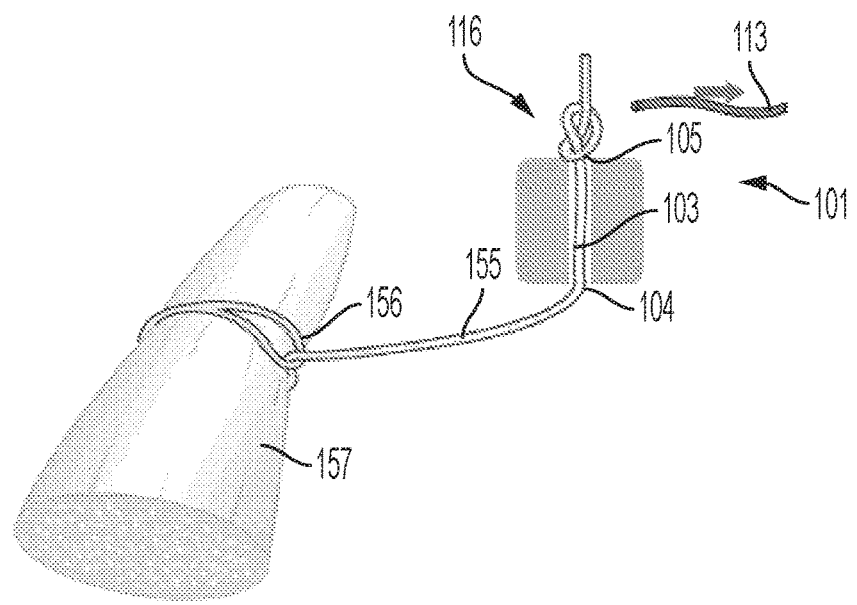

FIGS. 30 and 31 illustrates a second limb 155 of the surgical filament 104 having a distal loop 156 through which the second limb 155 is fed so as to engage around tissue 157, such as a tendon.

The surgical filament 104 is passed through the channel 103 of the anchor 101 and has the dilated knot 112 formed at the entrance 105 thereof.

FIG. 30 shows the dilater member 113, in this embodiment being a surgical filament, passing through the dilated knot 112 such that the dilated knot 112 can run around the dilater member 113 when pulled, thereby allowing the surgical filament 104 to run up through the channel 103 such that the second limb 155 tightens against the tissue 157 and the dilated knot 112 remains in place.

FIG. 31 shows the dilater member 113 having been pulled from the dilated knot 112 thereby causing the dilated knot 112 to strangulate at the entrance 105 to form a stopper knot 116 which cannot pass through the entrance 105 the channel.

FIGS. 32-39 shows further meniscal repair apparatus and technique comprising anchor toggles 132 each of which may similarly comprise a cylindrical body 133 defining the channel 103 therethrough between the first entrance 105 and a second entrance 106. The second entrance 106 may take the form of the aforedescribed side entrance 138 and the first entrance 105 may form a side notch 158.

Each anchor toggle 132 may similarly comprise a distal taper 134 for aiding insertion.

In the embodiment shown, the surgical filament 104 runs in and out of the side notch 158 and side entrance 138 of each adjacent anchor toggle 132 to thereby form two loops.

Figure 35:
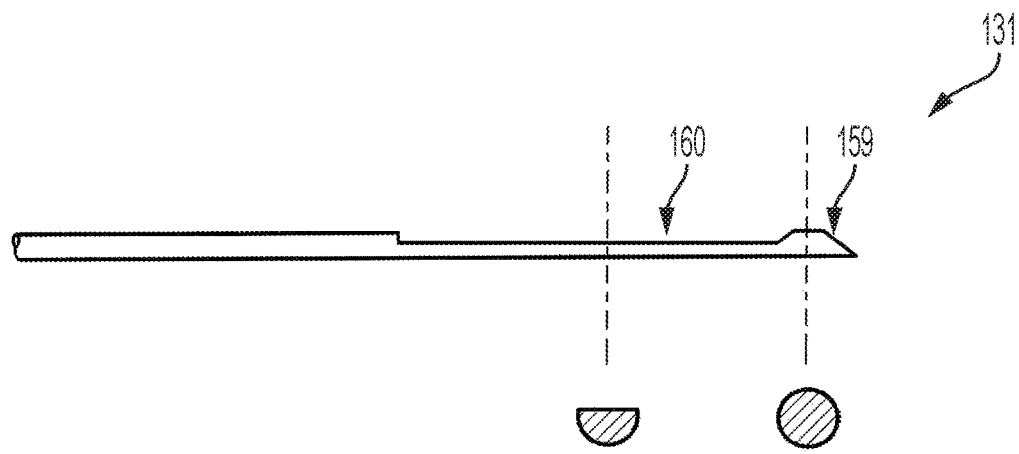
FIGS. 35-37 illustrate a side view of an insertion rod of the meniscal repair apparatus of FIG. 32-33.
Figure 36:
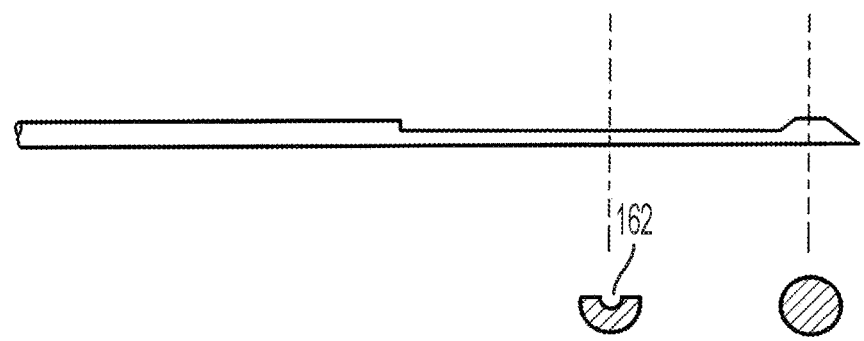
Figure 37:
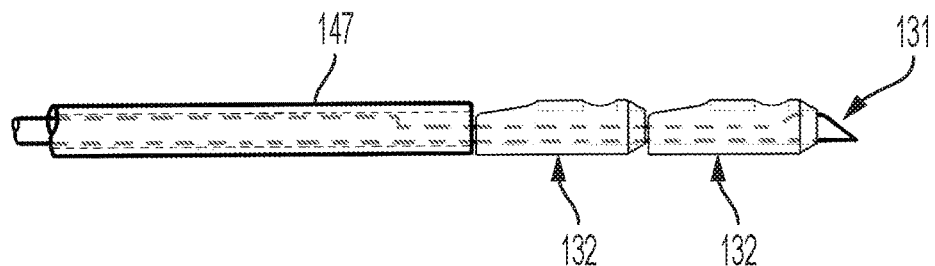

FIGS. 35 and 36 show the insertion rod 131 which inserts through the cannulated rod 147 to engage the anchor toggles 132 at a distal end thereof in the manner shown in FIG. 37.

The insertion rod 131 may define a distal tip 159 and a proximal neck portion 160. As shown in FIGS. 35 and 36, the distal tip 159 may be circular in cross-section. With reference FIG. 35, the proximal neck portion 160 may be semicircular cross-section and with further reference to FIG. 36, the proximal neck portion 140 may further define a channel 161 therealong for accommodating the filament 104.

The tip 159 may be sharpened, such as by being cut at an angle is shown in FIGS. 35-38 to aid insertion through the meniscus 151.

Figure 38:
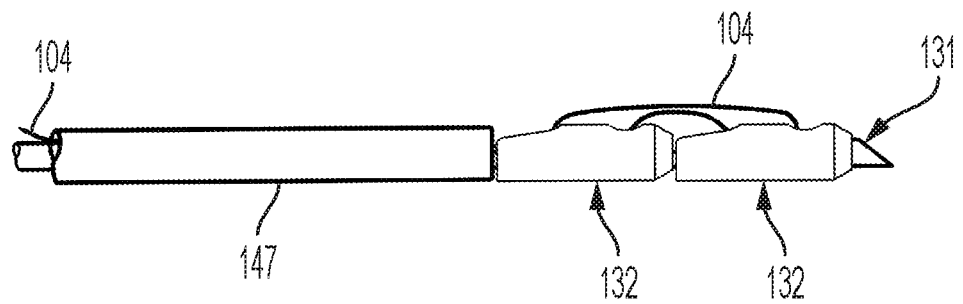
FIGS. 38-39 illustrate a surgical filament formation using the meniscal repair apparatus loaded with anchor toggles.
Figure 39:
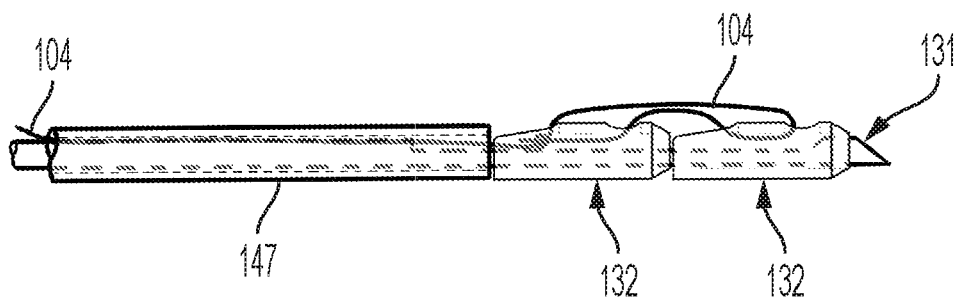

FIG. 38-39 illustrate the loading of the anchor toggles 132 to the insertion rod 131 and the way in which the filament is run through the cannulated rod 147 and through the anchor toggles 132 to form the aforedescribed two loops.

Figure 32:
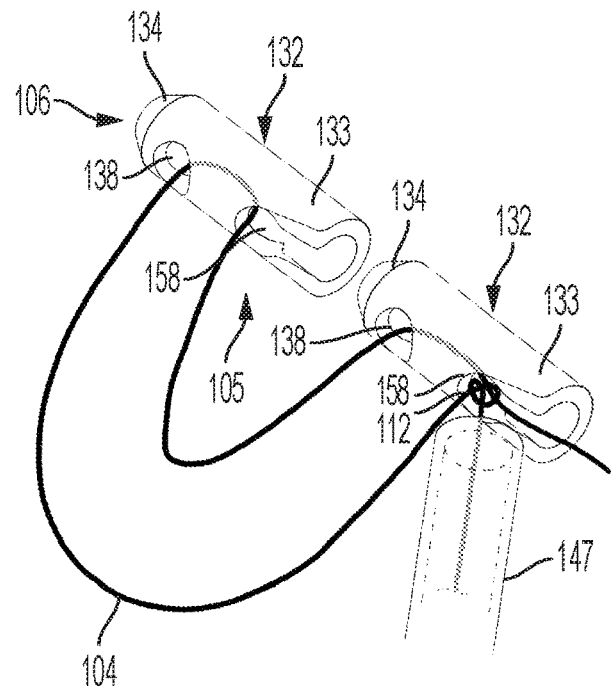
FIGS. 32-33 show further meniscal repair apparatus in accordance with an embodiment.
Figure 33:
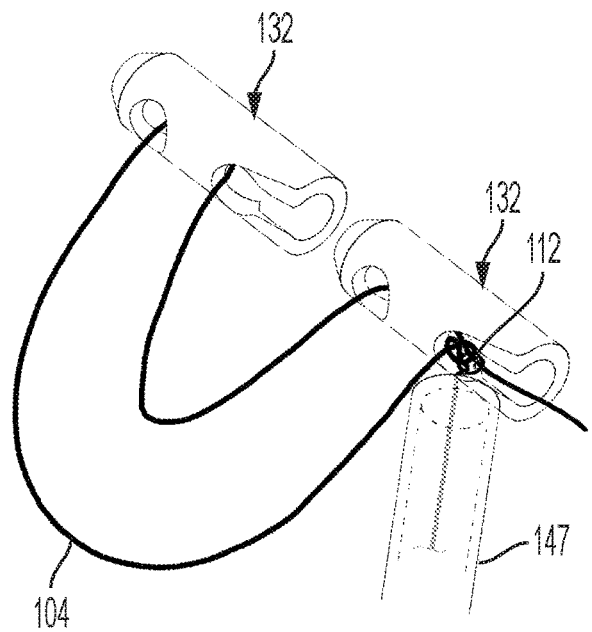
Figure 34:
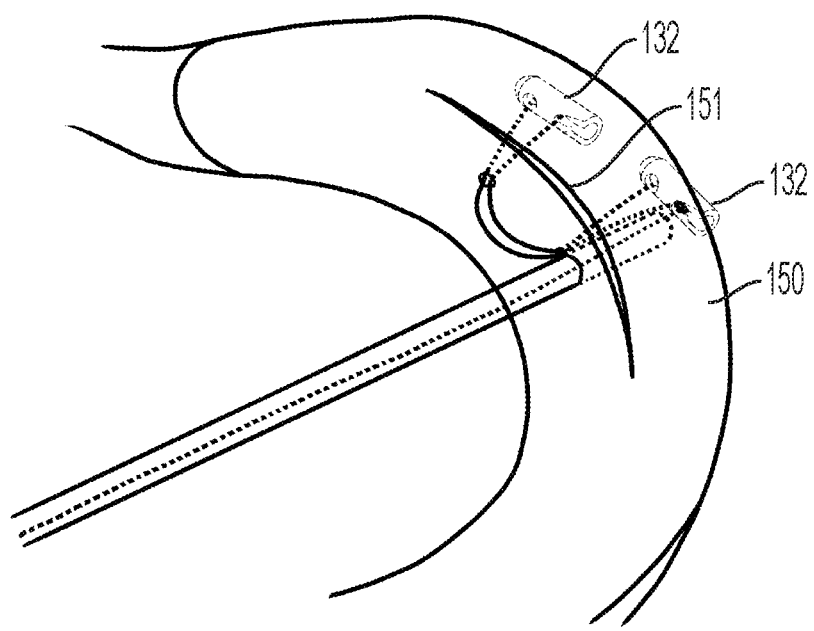
FIG. 34 illustrates meniscal repair using the apparatus of FIG. 32-33.

Specifically, the filament 104 may run through the channel 103 formed by the proximal anchor toggle 132, out from the side entrance 138 thereof, in through the side notch 158 of the distal anchor toggle 132, out from the side entrance 138 of the distal anchor toggle 132, back to the side notch 158 of the proximal anchor toggle where the dilated knot 112 is formed. FIG. 32 shows were the knot 112 comprises a single throw whereas FIG. 33 shows where the knot 112 comprises a double throw. It should be noted that the dilated knot 112 may be formed on the other limb of the filament 104 as compared to that which is shown in FIG. 32.

FIG. 35 illustrates how the toggles 132 are deployed in a similar manner as described above with reference to FIGS. 22-27.

In a similar manner as described above with reference to FIGS. 18 and 19, the cannulated rod 147 may comprise the dilator member 113 (such as one orthogonally, or longitudinally orientated or angled therebetween) which is twisted from the dilated knot 112 by rotating the cannulated rod 147 to form the tightened stopper knot 116 at the side notch 158 of the proximal anchor toggle 132 which cannot pass through the side notch 158. Alternatively, the dilator member 113 may take the form of the aforedescribed dilator suture 161.

In an alternative embodiment, and with reference to FIGS. 32 and 33 the dilated knot 112 may lie dilated and low profile along the insertion rod 131. In the embodiment wherein the insertion rod 131 comprises the longitudinal channel 162 therealong, the dilated knot 112 may lie within the channel 162. As such, when pulling a free limb of the filament 104 through the cannulated rod 147, the dilated knot 112 becomes strangulated and bunched up and catches within the side notch 158. Furthermore, the increased diameter of the dilated knot 112 prevents the dilated knot 112 from moving down the longitudinal channel 162 or at least from exiting the side entrance 138. In the embodiment shown in FIG. 33, the knot 112 may comprise more than one throw to have sufficient volume when strangulated to catch within the notch 158.

The foregoing description, for purposes of explanation, used specific nomenclature to provide a thorough understanding of the invention. However, it will be apparent to one skilled in the art that specific details are not required in order to practise the invention. Thus, the foregoing descriptions of specific embodiments of the invention are presented for purposes of illustration and description. They are not intended to be exhaustive or to limit the invention to the precise forms disclosed as obviously many modifications and variations are possible in view of the above teachings. The embodiments were chosen and described in order to best explain the principles of the invention and its practical applications, thereby enabling others skilled in the art to best utilize the invention and various embodiments with various modifications as are suited to the particular use contemplated. It is intended that the following claims and their equivalents define the scope of the invention.

The term "approximately" or similar as used herein should be construed as being within 10% of the value stated unless otherwise indicated.

The invention claimed is:

1. A surgical filament securement assembly comprising:
   a surgical filament,
   an insertion instrument comprising a dilater member and an insertion rod, wherein the dilater member is orientated substantially orthogonally with respect to an elongate axis of the insertion instrument and is formed by a longitudinal cut through the distal edge which transitions at a right angle to an orthogonal cut adjacent the dilater member, or orientated longitudinally with respect to an elongate axis of the insertion instrument and is formed by parallel longitudinal cuts either side thereof, and the insertion instrument further comprises an insertion rod which engages a bore of the anchor,
   an anchor extending along a longitudinal axis from a proximal face to a distal end, the anchor having a longitudinal bore centrally located and a longitudinal channel offset from a center of the anchor and extending therethrough between an entrance opening in the proximal face and an exit opening in a side of the anchor having exterior interference members,
   wherein the surgical filament is passed through the channel, the surgical filament tied to form a dilated knot having at least one throw around the dilater member at the entrance of the channel such that the surgical filament is able to run around the dilater member when a limb thereof is pulled in a first direction through the channel whilst the dilated knot remains in place at the entrance and wherein, when the dilater member is pulled out from within the dilated knot, the dilated knot itself strangulates to form a tightened stopper knot and wherein the channel has a diameter less than that of the tightened stopper knot such that the tightened stopper knot cannot pass through the entrance in the first direction.

2. An assembly as claimed in claim 1, wherein the anchor comprises a further channel for a further surgical filament through the proximal face.

3. An assembly as claimed in claim 2, wherein the dilater member passes through both dilated knots of the surgical filament and the further surgical filament.

4. An assembly as claimed in claim 1, wherein the dilater member comprises a dilater filament.

5. An assembly as claimed in claim 4, wherein the dilater member comprises a rigid member.

6. An assembly as claimed in claim 5, wherein the dilater member is orientated longitudinally with respect to the elongate axis of the anchor and wherein pulling the dilater member from the dilated knot comprises pulling the dilater member away from the anchor.

7. An assembly as claimed in claim 5, wherein the dilater member is orientated orthogonally with respect to the elongate axis of the anchor and wherein pulling the dilater member from the dilated knot comprises twisting the dilater member with respect to the anchor.

8. An assembly as claimed in claim 1, wherein the dilated knot is a single throw knot.

9. An assembly as claimed in claim 8, wherein the dilated knot is a overhand knot.

10. An assembly as claimed in claim 1, wherein the dilated knot is a multiple throw knot.

11. An assembly as claimed in claim 1, wherein the dilater member is integrally formed in a distal edge of the insertion instrument.

12. An assembly as claimed in claim 1, wherein the bore is non-coaxially adjacent the channel at the entrance.

13. An assembly as claimed in claim 1, wherein the bore comprises an interior dogleg around the channel and wherein the insertion rod transitions diagonally through the interior dogleg to engage the anchor.

14. An assembly as claimed in claim 13, wherein the insertion rod transitions diagonally from the side opening.

15. An assembly as claimed in claim 14, wherein the rod comprises a head which is able to fit diagonally through the interior dogleg as the rod passes from the proximal side opening.

16. An assembly as claimed in claim 15, wherein the head bears against opposite inner surfaces of the bore once past the dogleg.

17. An assembly as claimed in claim 13, wherein the insertion instrument comprises an orthogonal bearing face which bears against the proximal face of the anchor.

18. An assembly as claimed in claim 1, further comprising a distal anchor affixed to another limb of the surgical filament.

19. An assembly as claimed in claim 18, wherein the surgical filament is fixed through a side entrance of the distal anchor.

20. An assembly as claimed in claim 19, wherein the distal anchor comprises a bore therethrough for the slidable receipt of a tip of the insertion instrument therethrough.

21. An assembly as claimed in claim 20, wherein the tip is slidably retained within a coaxial rod and comprises a longitudinal member slidably retained within a side channel thereof, the longitudinal member comprising a bearing face which bears against the anchor.

* * * * *